United States Patent [19]

Shemano

[11] 3,946,112
[45] Mar. 23, 1976

[54] PHARMACEUTICALLY USEFUL BIS-BASIC ESTER AND THIOESTER DERIVATIVES

[75] Inventor: Irving Shemano, Cincinnati, Ohio

[73] Assignee: Richardson-Merrell Inc., Wilton, Conn.

[22] Filed: June 15, 1973

[21] Appl. No.: 370,291

[52] U.S. Cl.................................. 424/308; 424/274
[51] Int. Cl.²........................................ A61K 31/235
[58] Field of Search..................................... 424/308

Primary Examiner—Jerome D. Goldberg
Attorney, Agent, or Firm—L. Ruth Hattan; Eugene O. Retter; George W. Rauchfuss, Jr.

[57] ABSTRACT

Bis-basic ester derivatives of the following general formula are useful in the treatment of conditions of delayed hypersensitivity.

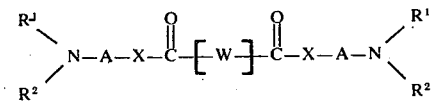

wherein [W] represents an aromatic polycyclic nucleus selected from fluoranthene, fluorene, fluoren-9-ol, fluoren-9-one, carbazole, or N-(lower)alkyl carbazole; X represents oxygen or sulfur; A represents a straight or branched alkylene chain of from 2 to 6 carbon atoms; and each of $R^1$ and $R^2$ is hydrogen, straight or branched lower alkyl of from 1 to 4 carbon atoms, or alkenyl of from 3 to 6 carbon atoms having the vinyl unsaturation in other than the 1-position; and pharmaceutically useful acid addition salts thereof.

9 Claims, No Drawings

PHARMACEUTICALLY USEFUL BIS-BASIC ESTER AND THIOESTER DERIVATIVES

FIELD OF INVENTION

This invention relates to the use of bis-basic ester and thioester derivatives of fluoranthene, fluorene, fluoren-9-ol, fluoren-9-one and carbazole.

DESCRIPTION OF PRIOR ART

Bis-basic ester and thioester derivatives of fluoranthene are disclosed in U.S. Pat. No. 3,531,489. Bis-basic ester derivatives of fluorene are disclosed in U.S. Pat. No. 3,647,860. Bis-basic ester derivatives of fluoren-9-ol are disclosed in U.S. Pat. No. 3,718,685. Bis-basic ester and thioester derivatives of fluoren-9-one are disclosed in U.S. Pat. No. 3,662,062. Each of these disclosures describes the compounds therein as being useful as antiviral agents and do not disclose or suggest the use of the compounds in treating conditions of delayed hypersensitivity.

SUMMARY OF THE INVENTION

Compounds of the following general Formula I are useful in treating conditions of delayed hypersensitivity:

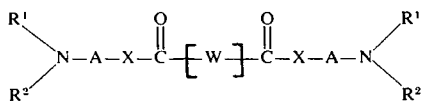

Formula I wherein [W] represents an aromatic polycyclic nucleus selected from fluoranthene, fluorene, fluoren-9-ol, fluoren-9-one, carbazole, or N-(lower)alkyl carbazole; X represents oxygen or sulfur; A represents a straight or brahcned alkylene chain of from 2 to 6 carbon atoms; and each of $R^1$ and $R^2$ represents hydrogen, straight or branched lower alkyl of from 1 to 4 carbon atoms, or alkenyl of 3 to 6 carbon atoms having the vinyl unsaturation in other than the 1-position. Pharmaceutically acceptable acid addition salts of the compounds of general Formula I are also included within the scope of this invention.

DETAILED DESCRIPTION OF INVENTION

It can be seen from the above general Formula I that the compounds disclosed herein are bis-basic ester or thioester derivatives of fluoranthene as represented by the following Formula II, or are bis-basic ester derivatives of fluorene, fluoren-9-ol, fluoren-9-one, carbazole or N-(lower)alkyl carbazole as represented by the following respective Formulas III – VI:

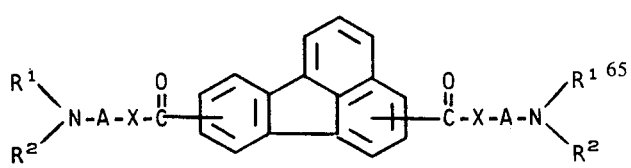

Formula II

| Y | Formula |
|---|---|
| —CH$_2$— | III |
| OH<br>\|<br>—CH— | IV |
| O<br>\|\|<br>—C— | V |
| R$^3$<br>\|<br>—N— | VI |

In the above general Formulas II to VI, X, A, $R^1$ and $R^2$ have the meanings defined hereinabove; and $R^3$ represents hydrogen or a lower alkyl group selected from methyl, ethyl, n-propyl or n-butyl.

In general Formula II one of the basic substituent groups as represented by

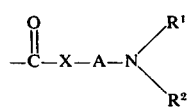

is attached to any one of the carbon atoms of the naphthalene portion of the tetracyclic nucleus and the other such basic substituent is attached to any one of the carbon atoms of the benzenoid ring of the tetracyclic nucleus. In general Formulas III to VI one of the basic substituents groups as represented by

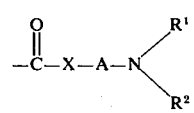

is attached to any one of the carbon atoms of one benzenoid ring of the tricyclic nuclei and the other such basic substituent is attached to any one of the carbon atoms of the other such benzenoid ring.

Illustrative examples of straight or branched alkylene groups which A may represent in general Formulas I to VI are ethylene, propylene, butylene, 2-ethylbutylene, 2-methylpropylene, and 3-methylpentylene.

Illustrative examples of straight or branched alkyl groups which $R^1$ and $R^2$ may represent in the above general Formulas I to VI are methyl, ethyl, n-propyl, n-butyl, isobutyl, and tert-butyl.

Pharmaceutically acceptable acid addition salts of the compounds of general Formula I include those of any suitable inorganic or organic acid. Illustrative suitable inorganic acids are hydrochloric, hydrobromic, sulfuric, and phosphoric acids. Illustrative suitable organic acids are lower aliphatic hydrocarbon monocarboxylic acids, such as, glycolic or lactic acid; lower aliphatic lower alkoxy-hydrocarbon monocarboxylic acids, such as, methoxyacetic or ethoxyacetic acids; lower aliphatic lower alkanoyl-hydrocarbon monocarboxylic acids, such as, pyruvic acid; lower aliphatic hydrocarbon dicarboxylic acids, such as, malonic, succinic, methylsuccinic, glutaric, α-methylglutaric, β-methylglutaric, itaconic, maleic citraconic, homocitraconic, or fumaric acid; lower aliphatic hydroxy hydrocarbon dicarboxylic acids, such as, malic or tartaric acid; lower aliphatic lower alkoxy-hydrocarbon dicarboxylic acids, such as, α,β-dimethoxysuccinic or ethoxymaleic acid; lower aliphatic hydrocarbon tricarboxylic acids, such as, aconitic or tricarballylic acid; lower aliphatic hydroxy-hydrocarbon tricarboxylic acids, such as, citric acid. Additionally organic sulfonic acids, such as lower alkane sulfonic acids, for example, methanesulfonic or ethanesulfonic acid, or lower hydroxyalkane sulfonic acids, for example, 2-hydroxyethane sulfonic acid are suitable. Particularly useful are pharmacologically acceptable acid addition salts with mineral acids, such as, hydrochloric acid. Mono- or di-acid salts may be formed, and the salts may be hydrated, for example, monohydrate, or substantially anhydrous.

Illustrative examples of compounds of this invention are bis(3-isopropylaminopropyl)fluoranthene-3,9-dicarboxylate, bis(3-dimethylaminobutyl)fluoranthene-3,9-dicarboxylate, bis(4-dipropylaminoethyl)-fluoranthene-3,8-dicarbothiolate, bis(3-dipropylaminopropyl)fluorene-2,7-dicarboxylate, bis(3-diallylaminopropyl)fluorene-2,8-dicarboxylate, bis(2-dimethylaminoethyl)fluoren-9-ol-2,7-dicarbothiolate, bis(5-diethylaminopentyl)fluoren-9-ol-2,7-dicarboxylate, bis(3-dimethylaminopropyl)-9-oxofluorene-2,6-dicarboxylate, bis(4-diisopropylaminobutyl)-9-oxofluorene,2,7-dicarboxylate, bis(5-diallylaminopentyl)carbazole-3,6-dicarboxylate, and N-ethyl bis(4-dibutylaminobutyl)carbazole-3,6-dicarbothiolate.

Introduction of an antigen, or a foreign substance, into an organism results in a specific immunological response changing the reactivity of the organism towards the antigen and substances closely resembling the antigen. This response is usually a heightened reactivity to the antigen. This heightened reactivity is due in part to the production of antibodies which can result in an immdeiate hypersensitivity and in part to a cell-mediated immunity which can result in delayed hypersensitivity. Cell-mediated immunity is dependent upon the presence of cells sensitized to antigen, primarily thymus-modified lymphocytes, which specifically interact with the antigen. Macrophages are also involved in the processing of antigen and in the effector mechanisms leading to delayed hypersensitivity.

The type of substances which elict delayed elicit are many and various. They may be organic chemicals, including drugs, simple chemical derivatives, or protein-containing antigens of micro-organisms, such as, bacteria, viruses, fungi or protozoa, or tissue antigens.

Conditions of delayed hypersensitivity are associated with numerous pathological disorders, for example, contact hypersensitivity in the skin rejection of tissue grafts or transplants, autoimmune diseases and certain infectious diseases. Such pathological disorders often involve, in addition to the cell-mediated delayed hypersensitivity responses, humoral antibody responses involving the production of antigen-specific antiboides. Generally, treatment of these disorders has been with immunosuppressive agents, such as, purine analogs, folic acid antagonists, alkylating agents and corticosteroids. Such agents have been found to be non-specific in their immunosuppressant effects, that is, they suppress both the humoral antibody and delayed (cell-mediated) hypersensitivity responses. [Drug Therapy 1, no. 4, pp. 3–16 (1971)]. The compounds disclosed herein are unique in that they suppress only the delayed hypersensitivity response without concurrent suppression of the humoral immune response.

The compounds disclosed herein suppress delayed hypersensitivity responses thereby rendering the compounds useful in patients in the treatment of conditions of delayed hypersensitivity resulting from infectious diseases, specifically tuberculosis, streptococcus, staphylococcus and pneumococcus diseases, typhoid fever, undulant fever, chancroid, whooping-cough and leprosy; toxoids and vaccines, particularly diphtheria toxoid and smallpox vaccination; contact hypersensitivity in the skin, specifically from nickel salts, primrose or poison ivy, poison oak and paraphenylene diamine; rejection of tissue grafts and transplants; and autoimmune diseases, specifically rheumatoid arthris, systemic lupus erythematosus, glomerular nephritis, rheumatic fever, ulcerative colitis, diabetes mellitus, pernicious anemia, coeliac disease, primary atypical pneumonia, Hashimoto's thyroiditis, multiple sclerosis, peripherial neuritis, pemphigus, Addison's disease and Grave's disease.

The utility of the compounds disclosed herein in the treatment of conditions of delayed hypersensitivity is manifested by the ability of the compounds to suppress delayed hypersensitivity reactions *in vitro* in the macrophage migration inhibition test (MMIT) and *in vivo* in the experimental allergic encephalomyelitis (EAE) test, which are well recognized tests for detecting agents or compounds effective in treating conditions of delayed hypersensitivity. *Immunology for Students of Medicine*, 3rd edition, 1970, F. A. Davis Company, pp. 498–500; Federation Proceedings 27, No. 1, pp. 3–15, (1968); Advances in Immunology 5, pp. 131–208 (1966).

As used herein, the term patient means warm blooded animals, particularly mammals and humans. The compounds disclosed herein may be administered to a patient orally, parenterally, or topically either alone or in the form of pharmaceutical preparations. Pharmaceutical preparations containing conventional pharmaceutical carriers and as active ingredients compounds of this invention can be employed in unit dosage forms such as solids, for example, tablets, capsules and pills, or liquid solutions, suspensions, or emulsions for oral and parenteral administration. The quantity of compound administered can vary over a wide range to provide from about 0.1 mg/kg (milligrams per kilogram) to about 200mg/kg of body weight of the patient per day, and preferably from about 1 mg/kg to 100mg/kg of body weight of the patient per day, to achieve the desired effect. Unit doses can contain from about 5 mg to 1.0 g of a compound of this invention and may be administered, for example, from 1 to 4 times daily.

The bis-basic esters and thioesters of general Formula I wherein [W] is fluoranthene, fluorenen, fluoren-9-one, carbazole, or N-(lower)alkyl carbazole can be prepared by the reaction of a compound of the formula

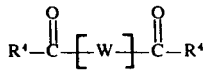   Formula VII wherein R⁴ is OH, halogen, such as, chlorine or bromine, or lower alkoxy, such as, methoxy or ethoxy and [W] represents fluoranthene, fluorene, fluoren-9-one, carbazole, and N-(lower)alkyl carbazole; with an aminoalkanol or an aminoalkylthiol of the formula

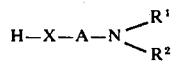   Formula VIII wherein A is a straight or branched alkylene chain of from 2 to 6 carbon atoms; X represents oxygen or sulfur; and each of $R^1$ and $R^2$ is hydrogen, straight or branched lower alkyl of from 1 to 4 carbon atoms, or alkenyl having the vinyl unsaturation in other than the 1-position. The esterification can be achieved by allowing the compound of Formula VII wherein R⁴ is hydroxy, to react with the appropriate aminoalkanol or aminoalkylthiol in an inert solvent in the presence of a catalyst and employing general methods for removing water from the reaction site. Preferred solvents are chloroform, isopropyl alcohol, dioxane, and toluene. The reaction may be catalyzed by the use of mineral acids including hydrochloric, sulfuric or certain organic acids, such as p-toluene-sulfonic acid. Methods whereby water can be removed from the reaction include the use of water scavengers such as the carbodiimides or by the azeotropic removal of water. The reaction will proceed at temperatures ranging from 50°–150°C over a period of 6 to 72 hours depending upon the solvent and catalyst.

Preferably, the esterification can be achieved by allowing the acid halide, where R⁴ in the above Formula VII is halogen, to react with the appropriate aminoalkanol or aminoalkylthiol. The esters and thioesters of this invention can be produced in a variety of inert solvents over a wide range of temperatures and reaction time. The solvents of choice include chloroform, dioxane, tetrahydrofuran, and the aromatic solvents such as benzene and toluene. In chloroform, the reaction is generally complete within 1 hour at the reflux temperature of the solvent, although the reaction time can range from 15 minutes to 3 days.

The bis-basic ester and thioester derivatives of general Formula I may also be prepared by a transesterification reaction in which a (lower) alkoxy ester, that is, a compound of Formula VII wherein R⁴ is, for example, methoxy or ethoxy, is reacted with the appropriate aminoalkanol or aminoalkylthiol under suitable conditions. This type of reaction is catalyzed by alkaline or acid catalyst and is reversible. The basic ester may be obtained by causing the equilibrium to be shifted by removing the aminoalkanol or aminoalkylthiol component or by employing a large excess of the aminoalkanol or aminoalkylthiol. Preferably, the reaction is carried out by removing the alkanol or alkylthiol component with the use of an alkaline catalyst. The alkanol or alkylthiol component may be removed by direct distillation or distillation with a suitable solvent. Suitable alkaline catalysts are alkali metals, such as, sodium or potassium; alkali lower alkoxides, such as, sodium methoxide or sodium ethoxide; or alkali amides such as lithium or sodium amide. Suitable solvents are those forming an azeotropic distillation mixture with the alkanol or alkylthiol component, for example, benzene or toluene, or a solvent which boils sufficiently higher than the alkanol or alkylthiol to permit its removal by distillation at a temperature below that of the boiling range of the solvent.

The bis-basic esters and thioesters of fluorene and fluoren-9-ol may be prepared by the reduction of the corresponding fluoren-9-one derivative. This reduction can be carried out either chemically or by hydrogenation in the presence of a catalyst except that (a) in the case of olefinic derivatives, methods must be used which do not destroy the unsaturation and (b) those primary and secondary amino derivatives which would rearrange to the corresponding amide derivatives as their free bases must be protected from rearrangement such as by maintaining them as their salts or protecting the amino groups with blocking groups during the reduction. Suitable blocking groups are carbobenzoxy, p-toluenesulfonyl, triphenylmethyl, and the like which can be removed after reduction by anhydrous hydrobromic acid, hydrobromic acid and phenol, hydrogenation under acidic conditions, and the like.

Hydrogenation of the fluorenone bis esters takes place in a stepwise fashion. Thus, at room temperature and at low pressure, one equivalent of hydrogen is rapidly absorbed to give the fluorenol derivative. Subsequent uptake of hydrogen is much slower so that if the fluorene derivative is desired, the reaction mixture should be heated to shorten the reaction periods. The hydrogenation can be carried out in any of a variety of solvents such as water, alcohols such as ethanol or methanol, dimethylformamide, or a mixture of these solvents. The fluorenone compound is hydrogenated in the acid addition salt form. Hydrogenation catalysts such as palladium or platinum, supported or unsupported, may be used in this hydrogenation.

The fluorenol compounds of this invention may be prepared by the chemical reduction of the corresponding base form of the fluorenone derivatives such as with sodium borohydride, lithium borohydride, and the like, at 0°–100°C for 10 minutes to 4 hours in a suitable solvent such as water, ethanol, and the like. The fluorenone bis-basic esters may be added to the borohydride reagent, either as the base dissolved in an organic solvent such as alcohols, or as the salt in an aqueous or aqueous-alcoholic solution. In the latter case, an excess of borohydride reagent should be used to compensate for reagent consumed by neutralization of the salt. Most primary and secondary amino compounds of this invention, in order to be reduced by this method, must be protected from rearrangement to the amide by blocking the amine groups to reaction as discussed above.

Additional methods for the preparation of bis-basic ester and/or thioester derivatives of fluoranthene, fluorene, fluoren-9-ol, and fluoren-9-one are set forth respectively in U.S. Pat. Nos. 3,531,489, 3,647,860, 3,718,685 and 3,662,062, and the appropriate portions of each patent are incorporated herein by reference thereto. The additional methods set forth in these disclosures may be employed to prepare the bis-basic ester and thioester derivatives of carbazole and N(lower)alkyl carbazole, that is, compounds of general Formula I wherein [W] is carbazole or N-(lower)alkyl carbazole.

The following specific Examples are illustrative of the compounds of general Formula I.

EXAMPLE 1

Bis(3-diethylaminopropyl)fluoranthene-3,9-dicarboxylate dihydrochloride

To 300 ml of chloroform are added 4.4 g of fluoranthene-3,9-dicarbonyl chloride and 3.51 g of 3-diethylaminopropanol and the resulting solution is refluxed for 1 hour. After cooling, a yellow solid product forms, which is filtered, washed with ether and crystallized from methanol-ethyl acetate to give bis(3-diethylaminopropyl)-fluoranthene-3,9-dicarboxylate dihydrochloride. M.P. 258°–260°C.

EXAMPLE 2

Bis(3-diethylaminopropyl)fluoranthene-3,8-dicarboxylate dihydrochloride

To 1 liter of chloroform is added 15.0 g (0.046 mole) of fluoranthene-3,8-dicarbonyl chloride and 12.2 g (0.093 mole) of 3-dimethylaminopropanol. During the addition of the latter reagent, a mildly exothermic reaction was noted. After about 15 minutes at reflux a yellow solid forms. The reaction mixture is refluxed overnight, cooled and the yellow product is filtered and crystallized from methanol-ethyl acetate to give bis(3-diethylaminopropyl)fluoranthene-3,8-dicarboxylate dihydrochloride. M.P. 259°–261°C.

EXAMPLE 3

Bis(3-diisopentylaminopropyl)fluoranthene-3,8-dicarboxylate dihydrochloride

To 700 ml of chloroform is added 10 g (0.033 mole) of fluoranthene-3,8-dicarbonyl chloride and 14.2 g (0.066 mole) of 3-diisopentylaminopropanol and the solution is refluxed for 3½ hours. The solution is concentrated, diluted with 400 ml of ethyl acetate, 300 ml of anhydrous ether and on cooling, a yellow product separates. The product is crystallized once from acetone and finally from butanone to give bis(3-diisopentylaminopropyl)fluoranthene-3,8-dicarboxylate dihydrochloride. M.P. 168°–171°C.

EXAMPLE 4

Bis(3-dibutylaminopropyl)fluoranthene-3,8-dicarboxylate dihydrochloride hemihydrate To 700 ml of chloroform is added 10.0 g (0.033 mole) of fluoranthene-3,8-dicarbonyl chloride and 12.4 g (0.066 mole) of 3-dibutylaminopropanol and the resulting solution is refluxed overnight. Upon cooling a solid forms which is crystallized from chloroform-ethyl acetate and twice from methanol-ethyl acetate. Further purification is achieved by dissolving the solid in water with subsequent conversion of the solid to the free base by the action of cold 3 N. aqueous potassium hydroxide, extraction of the free base with ether and after drying the ether solution converting the basic ester to the dihydrochloride salt with ethereal-hydrogen chloride. The product is crystallized from methanol-butanone-ether to give bis(3-dibutylaminopropyl)fluoranthene-3,8-dicarboxylate dihydrochloride hemidrate. M.P. 169°–173°C.

EXAMPLE 5

Bis(3-diallylaminopropyl)fluoranthene-3,8-dicarboxylate dihydrochloride

To 400 ml of chloroform is added 11.0 g (0.034 mole) of fluoranthene-3,8-dicarbonyl chloride and 10.7 g (0.068 mole) of 3-diallylaminopropanol and the solution is refluxed for 6 hours. The cloudy solution is filtered through dicalite and diluted with 500 ml of ether. The resulting yellow solid product is crystallized from methanol-acetone-ether to give bis(3-diallylaminopropyl)-fluoranthene-3,8-dicarboxylate dihydrochloride. M.P. 216.5°–219°C.

EXAMPLE 6

Bis(3-dipropylaminopropyl)fluoranthene-3,9-dicarboxylate dihydrochloride

To 500 ml of chloroform is added 9.8 g (0.03 mole) of fluoranthene-3.9-dicarbonyl chloride and 9.56 g (0.06 mole) of dipropylaminopropanol and the resulting solution is refluxed for 4 hours. On cooling, the product separates and is crystallized from methanol-ethyl acetate to give bis(3-dipropylaminopropyl)fluoranthene-3,9-dicarboxylate dihydrochloride. M.P. 247°–249°C.

EXAMPLE 7

Bis(3-diallylaminopropyl)fluoranthene-3,9-dicarboxylate

To 500 ml of chloroform is added 9.8 g (0.03 mole) of fluoranthene-3,9-dicarbonyl chloride and 9.3 g (0.06 mole) of 3-diallylaminopropanol and the solution is refluxed for 16 hours. The dihydrochloride salt is converted to the free base by treating the chloroform solution with saturated aqueous sodium bicarbonate, separation of the organic and water layer, drying the organic layer over anhydrous magnesium sulfate and finally removing the solvent in vacuo. The residue is dissolved in butanone and acidified with ethereal hydrogen chloride. The salt is crystallized twice from methanol-butanone or water-methanol-butanone, M.P. 229°–231°C, and converted back to the free base to give a yellow viscous oil of bis(3-diallylaminopropyl)-fluoranthene-3,9-dicarboxylate, $\lambda_{max}^{0.1\ NHCl}$ 229 m $\mu$, $E_1\ _{cm}\ ^{1\%}$ 605.

EXAMPLE 8

Bis(3-dipentylaminopropyl)fluoranthene-3,9-dicarboxylate

To 400 ml of chloroform is added 9.8 g (0.03 mole) of fluoranthene-3,9-dicarbonyl chloride and 18.9 g (0.06 mole) of 3-dipentylaminopropanol and the solution is refluxed for 16 hours. Purification is accomplished by the method described in Example 7. The dihydrochloride salt of the subject base melts at 148°–151°C and is converted to the free base as a yellow viscous oil after column chromatography, $\lambda_{max}^{CHCl_3}$ 301, $E_1\%_{cm}$ 643.

EXAMPLE 9

Bis(3-diethylaminopropyl)fluoranthene-3,9-dicarboxylate dihydrochloride

A toluene solution of 1 equivalent of dimethyl fluoranthene-3,9-dicarboxylate and 2.2 equivalents of 3- diethylaminopropanol containing a catalytic amount (ca 0.1 equivalent) of sodium methoxide is slowly distilled under an efficient distillation column until the rise in temperature of distillation indicates complete removal of the methanol being formed. Several periods of alternate reflux and distillation may be used rather than continuous slow distillation. The product is isolated by diluting the cooled reaction mixture with ether, washing several times with water, drying over anhydrous sodium sulfate, and precipitation of the dihydrochloride salt with ethereal hydrogen chloride. The precipitated salt is collected and recrystallized from methanol-ethyl acetate to give bis(3-diethylaminopropyl)fluoranthene-3,9-dicarboxylate dihydrochloride.

EXAMPLE 10

Bis(2-diethylaminoethyl)fluoranthene-3,9-dicarbothiolate dihydrochloride

To 400 ml of chloroform is added 9.8 g (0.03 mole) of fluoranthene-3,9-dicarbonyl chloride and 10.2 g (0.06 mole) of 2-diethylaminoethanethiol and the solution is refluxed for 16 hours. Purification is accomplished by the method described in Example 7. The product is crystallized 3 times from methanol-butanone to give bis(2-diethylaminoethyl)fluoranthene-3,9-dicarbothiolate dihydrochloride. M.P. 259.5°–261.5°C.

EXAMPLE 11

A suspension of 30.5 g (0.10 mole) of 9-oxofluorene-2,7-dicarbonyl chloride in 1 liter of dry chloroform (ethanol-free) is stirred and threated all at once with 37.5 g (0.20 mole) of dry 3-di-n-butylaminopropanol causing a mildly exothermic reaction. The resulting mixture is stirred and refluxed for 2 hours, cooled to room temperature, filtered and the filtrate washed 3 times with 250-ml portions of saturated sodium bicarbonate solution. The chloroform solution is then washed with water and saturated sodium chloride solution, dried over anhydrous sodium sulfate and filtered. Most of the solvent is removed from the filtrate on a steam bath under vacuum and the residue dissolved in butanone. This solution is made acid to Congo Red with ethereal HCl causing the product to precipitate as a yellow crystalline solid. The bis(3-di-n-butylaminopropyl)-9-oxofluorene-2,7-dicarboxylate dihydrochloride is filtered, recrystallized from butanone-methanol (just sufficient methanol to dissolve the solid in the boiling solution) and dried. The compound on standing in the atmosphere forms a monohydrate. M.P. 178.5°–179.5°C.

EXAMPLE 12

Bis(3-diethylaminopropyl)-9-oxofluorene-2,5-dicarboxylate dihydrochloride

To 5.55 g (0.018 mole) of 9-oxofluorene-2,5-dicarbonyl chloride, in 200 ml of chloroform is added 4.78 g (0.036 mole) of 3-diethylaminopropanol and the resulting solution is refluxed for 3 hours, and diluted with methyl ethyl ketone. On cooling a precipitate forms which is recrystallized from methanol-ethyl acetate to give bis(3-diethylaminopropyl)-9-oxofluorene-2,5-dicarboxylate dihydrochloride. M.P. 203°–205°C.

EXAMPLE 13

Bis(6-diethylaminohexyl)-9-oxofluorene-2,7-dicarboxylate

When in the procedure of Example 11, 6-diethylaminohexanol is substituted for 3-di-n-butylaminopropanol, bis(6-diethylaminohexyl)-9-oxofluorene-2,7-dicarboxylate is obtained. M.P. 214.5°–216.5°C (dec.).

EXAMPLE 14

Bis(3-di-n-butylaminopropyl)-9-oxofluorene-2,7-dicarbothiolate

When in the procedure of Example 11 3-di-n-butylaminopropanethiol is used in place of 3-di-n-butylaminopropanol, bis(3-di-n-butylaminopropyl)-9-oxofluorene-2,7-dicarbothiolate is obtained.

EXAMPLE 15

Bis(5-dimethylamino-2,2-dimethylpentyl)-9-oxofluorene-2,7-carboxylate dihydrochloride When in the procedure of Example 11, 5-dimethylamino-2,2-dimethylpentanol is substituted for 3-di-n-butylaminopropanol, bis(5-dimethylamino-2,2-dimethylpentyl)-9-oxofluorene-2,7-carboxylate dihydrochloride is obtained, M.P. 204°–206°C as the hemihydrate.

EXAMPLE 16

Bis(5-dimethylamino-2,2-dimethylpentyl)fluorene-2,7-dicarboxylate dihydrochloride A solution of 20.0 g (0.0321 mole) of bis(5-dimethylamino-2,2-dimethylpentyl)-9-oxofluorene-2,7-dicarboxylate dihydrochloride in water (total volume = 240 cc.) is hydrogenated over 8.0 g of 10% palladium on charcoal for 2 days at 53°C on a Parr hydrogenation apparatus. The reaction mixture is decanted from the catalyst, filtered through filtered acid, treated with charcoal and again filtered. This solution is made basic to phenolphthalein with 20% NaOH and extracted 3 times with $CHCl_3$. The combined extracts were washed twice with water, dried over anhydrous $Na_2SO_4$, filtered and the filtrate made acid to Congo Red with ethereal HCl. Most of the solvent is removed on the steam bath under vacuum and the resulting solid recrystallized from methanol-ether and from absolute ethanol. Bis(5-dimethylamino-2,2-dimethylpentyl)fluorene-2,7-dicarboxylate dihydrochloride thus obtained is dried for 4 hours under high vacuum at 80°C. M.P. 294°–295°C (gas evolution).

EXAMPLE 17

Bis(3-diethylaminopropyl)-9-ethylcarbazole-3,6-dicarboxylate dihydrochloride

To 250 ml of isopropanol is added 10.0 g (0.035 mole) of 9-ethylcarbazole-3,6-dicarboxylic acid, 21.2 g (0.14 mole) of 3-diethylaminopropylchloride and 0.5 ml of 60% aqueous benzyltrimethylammonium chloride. The solution is heated at reflux for 2 hours with stirring and then allowed to stir overnight at room temperature. Addition of ether to the reaction mixture gives a crystalline product which is recrystallized twice from methanol-acetone to give bis(3-diethylaminopropyl)-9-ethylcarbazole-3,6-dicarboxylate dihydrochloride. M.P. 233°–234°C.

EXAMPLE 18

Bis(5-amino-2,2-dimethylpentyl)-9-ethylcarbazole-3,6-dicarboxylate dihydrochloride A solution of 2 molar equivalents of 5-amino-2,2-dimethyl-1-pentanol as the hydrochloride salt and one molar equivalent of 9-ethylcarbazole-3,9-dicarbonyl chloride in a sufficient volume of chloroform is refluxed for several hours. The product, bis(5-amino-2,2-dimethylpentyl)-9-ethylcarbazole-3,6-dicarboxylate dihydrochloride, is purified by recrystallization from methanol-ethyl acetate.

EXAMPLE 19

Bis(3-diethylaminopropyl)carbazole-2,6-dicarboxylate

Bis(3-diethylaminopropyl)carbazole 2,6-dicarboxylate is prepared by the esterification of carbazole-2,6-dicarboxylic acid, the synthesis of which is reported by D. Brooke and S. Plant, J. Chem. Soc., 2212 (1956), according to the procedure of Example 17.

Additional examples for the preparation of bis-basic ester and/or thioester derivatives of fluoranthene, fluorene, fluoren-9-ol and fluoren-9-one are set forth respectively in U.S. Pat. Nos. 3,531,489, 3,647,860, 3,718,685 and 3,662,062 and the appropriate examples of each of these patents are incorporated herein by reference thereto.

The following Examples are illustrative of pharmaceutical preparations containing as active ingredients compounds of general Formula I.

EXAMPLE 20

An illustrative composition for tablets is as follows:

|     |                                                         | Per Tablet |
| --- | ------------------------------------------------------- | ---------- |
| (a) | bis(3-diethylaminopropyl)fluoranthene-3,9-dicarboxylate dihydrochloride | 100.0 mg   |
| (b) | wheat starch                                            | 15.0 mg    |
| (c) | lactose                                                 | 33.5 mg    |
| (d) | magnesium stearate                                      | 1.5 mg     |

A portion of the wheat starch is used to make a granulated starch paste which together with the remainder of the wheat starch and the lactose is granulated, screened and mixed with the active ingredient, that is, (a), and the magnesium stearate. The mixture is compressed into tablets weighing 150 mg each.

EXAMPLE 21

An illustrative composition for a parenteral injection is the following wherein the quantities are on a weight to volume bases.

|     |                                                         | amount    |
| --- | ------------------------------------------------------- | --------- |
| (a) | bis(3-diethylaminopropyl)-9-oxofluorene-2,5-dicarboxylate dihydrochloride | 100.0 mg  |
| (b) | sodium chloride                                         | q.s.      |
| (c) | water for injection to make                             | 10.0 ml   |

The composition is prepared by dissolving the active ingredient, that is (a), and sufficient sodium chloride in water for injection to render the solution isotonic. The composition may be dispensed in a single ampule containing 100 mg of the active ingredient for multiple dosage or in 10 ampules for single dosage.

EXAMPLE 22

An illustrative composition for hard gelatin capsules is as follows:

|     |                                                         | Per Capsule |
| --- | ------------------------------------------------------- | ----------- |
| (a) | bis(5-dimethylamino-2,2-dimethylpentyl)fluorene-2,7-dicarboxylate dihydrochloride | 200.0 mg    |
| (b) | talc                                                    | 35.0 mg     |

The composition is prepared by passing the dry powders of (a) and (b) through a fine mesh screen and mixing them well. The power is then filled into No. 0 hard gelatin capsules at a net fill of 235 mg per capsule.

EXAMPLE 23

An illustrative composition for pills is as follows:

|     |                                                         | Per Pill  |
| --- | ------------------------------------------------------- | --------- |
| (a) | bis(3-diethylaminopropyl)-9-ethylcarbazole-3,6-dicarboxylate dihydrochloride | 200 mg    |
| (b) | corn starch                                             | 130 mg    |
| (c) | liquid glucose                                          | 20 ml     |

The pills are prepared by blending the active ingredient (a) and the corn starch then adding the liquid glucose with thorough kneading to form a plastic mass from which the pills are cut and formed.

It is claimed:

1. A method of treating conditions of delayed hypersensitivity which comprises administering to a patient in need thereof a compound selected from the formula $$\underset{R^2}{\overset{R^1}{>}}N-A-X-\overset{O}{\underset{\|}{C}}-[W]-\overset{O}{\underset{\|}{C}}-X-A-N\underset{R^2}{\overset{R^1}{<}}$$

wherein [W] represents an aromatic polycyclic nucleus selected from fluoranthene, fluorene, fluoren-9-ol, or fluoren-9-one X is selected from oxygen or sulfur; A is selected from a straight or branched alkylene chain of from 2 to 6 carbon atoms; and each of $R^1$ and $R^2$ is selected from hydrogen, straight or branched lower alkyl of from 1 to 4 carbon atoms or alkenyl of 3 to 6 carbon atoms having the vinyl unsaturation in other than the 1-position; and pharmaceutically acceptable acid addition salts thereof, in an amount effective to suppress delayed hypersensitivity.

2. A method of claim 1 wherein [W] is fluoranthene.

3. A method of claim 2 wherein the compound is bis-(3-dimethylaminopropyl)fluoranthene-3,9-dicarboxylate, or a pharmaceutically acceptable acid addition salt thereof.

4. A method of claim 2 wherein the compound is bis-(3-diethylaminopropyl)fluoranthene-3,9-dicarboxylate, or a pharmaceutically acceptable acid addition salt thereof.

5. A method of claim 1 wherein [W] is fluorene.

6. A method of claim 5 wherein the compound is bis-(3-dibutylaminopropyl)fluorene-2,7-dicarboxylate, or a pharmaceutically acceptable acid addition salt thereof.

7. A method of claim 1 wherein [W] is fluoren-9-one.

8. A method of claim 1 wherein the compound is bis-(3-diethylaminopropyl)-9-oxofluorene-2,7-dicarboxylate, or a pharmaceutically acceptable acid addition salt thereof.

9. A method of claim 7 wherein the compound is bis-(6-diethylaminohexyl)-9-oxofluorene-2,7-dicarboxylate, or a pharmaceutically acceptable acid addition salt thereof.

* * * * *

UNITED STATES PATENT AND TRADEMARK OFFICE
CERTIFICATE OF CORRECTION

PATENT NO. : 3,946,112
DATED : March 23, 1976
INVENTOR(S) : Irving Shemano

It is certified that error appears in the above-identified patent and that said Letters Patent are hereby corrected as shown below:

Column 1, line 40, "brahcned" should read "branched". Column 2, line 46, "oxofluorene,2,7-" should read "oxofluorene-2,7-". Column 3, line 56, "immdeiate" should read "immediate"; line 64, "elicit delayed elicit are" should read "elicit delayed hypersensitivity are"; Column 4, line 8, "antiboides" should read "antibodies"; line 32, "arthris" should read "arthritis"; line 36, "peripherial" should "peripheral". Column 5, line 5, "fluorenen" should read "fluorene". Column 8, line 2, "hemidrate" should read "hemihydrate"; line 9, "fluroanthene" should read "fluoranthene". Column 9, line 35, "threated" should read "treated". Column 10, line 40, "filtered acid" should read "filter aid".

Signed and Sealed this

Tenth Day of May 1977

[SEAL]

Attest:

RUTH C. MASON
Attesting Officer

C. MARSHALL DANN
Commissioner of Patents and Trademarks